United States Patent
Uutela et al.

(10) Patent No.: US 7,294,785 B2
(45) Date of Patent: Nov. 13, 2007

(54) PATIENT CABLE FOR MEDICAL MEASUREMENTS

(75) Inventors: Kimmo Uutela, Helsinki (FI); Sami Miettinen, Helsinki (FI); Tapani Niklander, Espoo (FI); Juha Virtanen, Helsinki (FI)

(73) Assignee: GE Healthcare Finland Oy (FI)

( * ) Notice: Subject to any disclaimer, the term of this patent is extended or adjusted under 35 U.S.C. 154(b) by 129 days.

(21) Appl. No.: 10/871,530

(22) Filed: Jun. 18, 2004

(65) Prior Publication Data
US 2005/0027191 A1 Feb. 3, 2005

(30) Foreign Application Priority Data
Jun. 19, 2003 (EP) .................................. 03396061

(51) Int. Cl.
*H01R 9/05* (2006.01)
*A61B 5/05* (2006.01)

(52) U.S. Cl. ...................... 174/74 R; 600/421; 600/411

(58) Field of Classification Search ................ 600/421, 600/411, 413, 418; 174/74 R, 88 R
See application file for complete search history.

(56) References Cited

U.S. PATENT DOCUMENTS

| | | |
|---|---|---|
| 4,301,428 A | 11/1981 | Mayer |
| 4,951,672 A | 8/1990 | Buchwald et al. |
| 5,523,534 A | 6/1996 | Meister et al. |
| 5,693,045 A * | 12/1997 | Eggers .......................... 606/50 |
| 6,032,063 A * | 2/2000 | Hoar et al. .................. 600/372 |
| 2003/0135110 A1 | 7/2003 | Luessler |
| 2004/0034296 A1 | 2/2004 | Ristolainen |

FOREIGN PATENT DOCUMENTS

| | | |
|---|---|---|
| DE | 199 22 999 | 11/2000 |
| WO | WO01-97688 | 12/2001 |
| WO | WO 02/13689 | 2/2002 |

OTHER PUBLICATIONS

Patent Abstracts of Japan, vol. 016, No. 277, Jun. 22, 1992 & JP 04 071536 (Toshiba Corp.) Mar. 6, 1992.
Recording of EEG during fMRI Experiments: Patient Safety, Louis Lemieux et al., Magnetic resonance in Medicine, 38:943-952, 1997.
Investigation of the Factors Responsible for Burns During MRI, Dempsey et al., Journal of Magnetic Resonance Imaging 13:627-631 (2001).
EP Communication dated Oct. 27, 2005.

\* cited by examiner

*Primary Examiner*—Chau N. Nguyen
(74) *Attorney, Agent, or Firm*—Andrus, Sceales, Starke & Sawall, LLP

(57) ABSTRACT

The invention relates to a patient cable for medical measurements performed in connection with Magnetic Resonance Imaging (MRI). In order to eliminate the risk of thermal injuries without compromising the signal-to-noise ratio more than what is required for patient safety, the patient cable comprises two successive cable elements having different resistance characteristics. The second cable element, which is connected by the first cable element to the patient, has a total resistance increased from a normal high-conductivity resistance value of a patient cable to suppress antenna resonances in the second cable element. The first cable element, which is connected to the electrodes on the skin of the patient, has a total resistance substantially greater than that of the second cable element to prevent electromagnetically induced currents from flowing to the patient and to prevent excessive heating of the cable by electromagnetic induction.

11 Claims, 1 Drawing Sheet

PATIENT CABLE FOR MEDICAL MEASUREMENTS

CROSS REFERENCE TO RELATED APPLICATION

The present application claims priority from European Patent Application No. 03396061.8, filed Jun. 19, 2003.

1. Field of the Invention

The present invention relates generally to patient cables or electrode lead wires used in medical measurements for measuring bioelectric signals. More particularly, the present invention relates to patient cables suitable for Magnetic Resonance Imaging (MRI).

2. Background of the Invention

As is known, MRI (Magnetic Resonance Imaging) is a technique used for getting images of a body without the use of X-rays. In MRI, the patient is placed within a rapidly changing magnetic field created by the MRI device. Radio waves are simultaneously transmitted to the patient, and images of the interior of the body are obtained by means of a computer analysis of the radio waves received from the patient. During the imaging, the condition of the patient is constantly monitored. This includes the monitoring of the ECG signal of the patient, for example.

The distance between the electrodes attached on the skin of the patient and the physiological monitoring device, such as an ECG monitor, is rather long as the patient is inside the MRI apparatus and the monitoring device is typically clearly apart from the MRI device. The practical solutions for transferring the biosignals from the electrodes to the monitoring device are twofold: the actual measurement electronics are either at the monitoring device or in the proximity of the patient, i.e. inside the MRI device. In the former case a long cable connects the electrodes to the measurement electronics, while in the latter case the measurement results are transferred through an optic fiber to the monitoring device.

A major drawback relating to the implementation based on the use of an optic fiber is the difficulty in introducing the measurement electronics into the MRI device, since the measurement electronics must be compatible with the MRI environment. Therefore, special circuits and components must be used inside the MRI device. Furthermore, as the power needed by the measurement electronics cannot be supplied through the optic fiber, the measurement electronics inside the MRI device must be battery-supplied.

Due to the above difficulties related to the introducing of the measurement electronics into the MRI device, the approach of using long patient cables for connecting the electrodes to the measurement electronics located at the monitoring device is widely used.

In ECG monitoring the voltage differences caused by the heart between the electrodes are measured by an ECG monitor. The electric signals generated by the heart are weak, typically from 0.5 mV to 2 mV. In order to achieve a low interference level, the electrodes are connected to the monitor by high-conductive cables. The total resistance of these cables is of the order of a few ohms only. However, monitoring in an MRI environment sets certain requirements for the cables. This is discussed briefly in the following.

In MRI imaging, strong RF (Radio Frequency) radiation is used, the frequency of which is typically between 8 MHz and 130 MHz, depending on the strength of the magnetic field. As the patient cables are in this magnetic field, electromotive forces may induce to the cable through different mechanisms. This results in heating of the electrodes/cables, and possible also in currents flowing through the patient. The MRI environment therefore involves an increased risk of thermal injury. These mechanisms are discussed in the article Lemieux et al., *Recording of EEG during fMRI Experiments: Patient Safety*, Magnetic Resonance in Medicine, 38:943-952, 1997. In this article a minimum value of 13 kOhm is estimated for a current-limiting resistor to be fitted in each electrode lead to limit the currents induced, and to guarantee patient safety. It is also recommended in the article that the current-limiting resistors are placed as near as possible to the electrodes.

Thus, although the nursing staff is instructed in the use of the cables, for example by instructing them to avoid cable loop formation that results in larger currents induced, the cables should always have a sufficient resistance to protect the patient from thermal injury.

One alternative for obtaining a sufficient resistance for the cable is to use high-conductivity material for the cable conductor and to add resistor elements along the length of the cable. Patient cables like this are disclosed in the above-mentioned article by Lemieux et al., and also in U.S. Pat. No. 4,951,672 (Buchwald et al.), for example.

Another alternative for obtaining a sufficient resistance is to use semi-conductive leads, such as carbon fibers, whereby the higher-than-normal resistance can be more evenly distributed across the length of the cable. Different cable structures based on semi-conductive materials are disclosed in U.S. Pat. No. 5,523,534 (Meister et al.) and U.S. Pat. No. 6,032,063 (Hoar et al.), and in German Offenlegungsschrift DE-19922999-A1, for example. These cables are safe as long as the cable resistance per unit of length is high enough. However, for a long cable the total resistance becomes easily so high that the signal-to-noise ratio of the measurement is significantly degraded.

It has also been discovered recently that limiting the currents that flow to the patient through the cable is not enough to eliminate the risk of thermal injury. This is due to a so-called antenna effect, which may cause a strong heating effect on the skin of the patient. As is discussed in the article Dempsey et al.: *Investigation of the Factors Responsible for Burns During MRI*, Journal of Magnetic Resonance Imaging 13:627-631 (2001), the antenna effect may sometimes be a major factor in causing thermal injury. Extended monitoring cables behave as RF wire antennae that are sensitive to the electric component of the RF radiation used in an MRI device. Resonant antennae exhibit current and voltage standing wave patterns, which result in high RF fields at the ends of the cable. Thermal injury may in this way be caused even without direct contact with the skin of the patient. The strength of the antenna effect depends on the length of the cable and on the wavelength of the RF radiation: if the effective length of the cable is substantially smaller than the wavelength, the antenna effect remains weak. As the wavelength depends on the magnet used and as the effective length of the antenna (i.e. cable) depends, in addition to its physical length, on the environment, no accurate limit values can be given for eliminating the antenna effect. However, in low-conductivity cables the antenna effect is weak.

A drawback relating to the above-described known cable structures is that the antenna effect is suppressed only in cables having a high total resistance, whereby the signal-to-noise ratio of the measurement is highly compromised. In other words, the prior art cable structures suitable for suppressing the above-described heating mechanisms have not been designed to optimize the measurement with respect to the signal-to-noise ratio.

The objective of the invention is to provide a novel patient cable that eliminates the above drawback.

SUMMARY OF THE INVENTION

The objective of the present invention is to bring about a novel patient cable suitable for use in MRI environments, Which effectively eliminates the risk of thermal injuries without compromising the signal-to-noise ratio more than what is required for patient safety.

The patient cable of the present invention comprises two successive elements: a first element, which is, when used, substantially in its entirety inside the MRI device, and a second element that connects the first element to the measuring electronics located at the monitoring device. The cable elements are semi-conductive with different resistance characteristics so that the first element tackles the problem related to electromagnetically induced currents. The starting point of the second element is a normal high-conductivity non-MRI cable, which would provide the best possible signal-to-noise ratio for the measurement. However, the total resistance of the second element is increased from this normal value to a level that is enough to suppress antenna resonances. Thus the first element, which is in a high RF field, serves to prevent injuries caused by induction heating and electromagnetically induced currents flowing through the patient. The resistance of the second element is clearly insufficient for this purpose, even if the whole cable were made of the second element only. However, the resistance of the second cable element is enough to suppress antenna resonances.

Therefore, there are lower limits for the total resistances of each of the two elements: the total resistance of the first element is limited by the minimum resistance needed to prevent patient currents and excessive cable heating caused by electromagnetic induction, while the total resistance of the second element is limited by the minimum resistance needed to suppress antenna resonances. The resistances are preferably minimized given the above limitations.

Thus one aspect of the invention is providing a patient cable adapted for conducting bioelectric signals from at least one medical electrode on a subject in an MRI study to a physiological monitoring device. The patient cable comprises a first elongated cable element having a first end and a second end, the first end being adapted for connecting the first cable element to said at least one electrode, and a second elongated cable element having a first end and a second end, the first end being adapted for connecting the second cable element to the second end of the first cable element for conducting the bioelectrical signals from the first cable element to the physiological monitoring device. The second cable element has a total resistance which is increased from a normal high-conductivity resistance value of a patient cable to suppress antenna resonances in the second cable element, whereas the first cable element has a total resistance substantially greater than that of the second cable element to prevent electromagnetically induced patient currents and heating of the cable by electromagnetic induction.

The invention provides a safe patient cable for measuring bioelectric signals in MRI environments, without excessively compromising the signal-to-noise ratio of the measurement.

Another aspect of the invention is that of providing a patient cable element adapted for conducting bioelectric signals originated from at least one medical electrode on a subject inside an MRI device to a physiological monitoring device. The cable element comprises a first end provided with connector means for connecting the cable element to another cable element outputting bioelectric signals from inside of an MRI device. The cable element has a total resistance that is increased from a normal high-conductivity resistance value of a patient cable to suppress antenna resonances in the cable element.

Other features and advantages of the invention will become apparent by reference to the following detailed description and accompanying drawings.

BRIEF DESCRIPTION OF THE DRAWINGS

In the following, the invention and its preferred embodiments are described more closely with reference to the examples shown in the appended drawing, wherein.

DETAILED DESCRIPTION OF THE INVENTION

Figure 1:
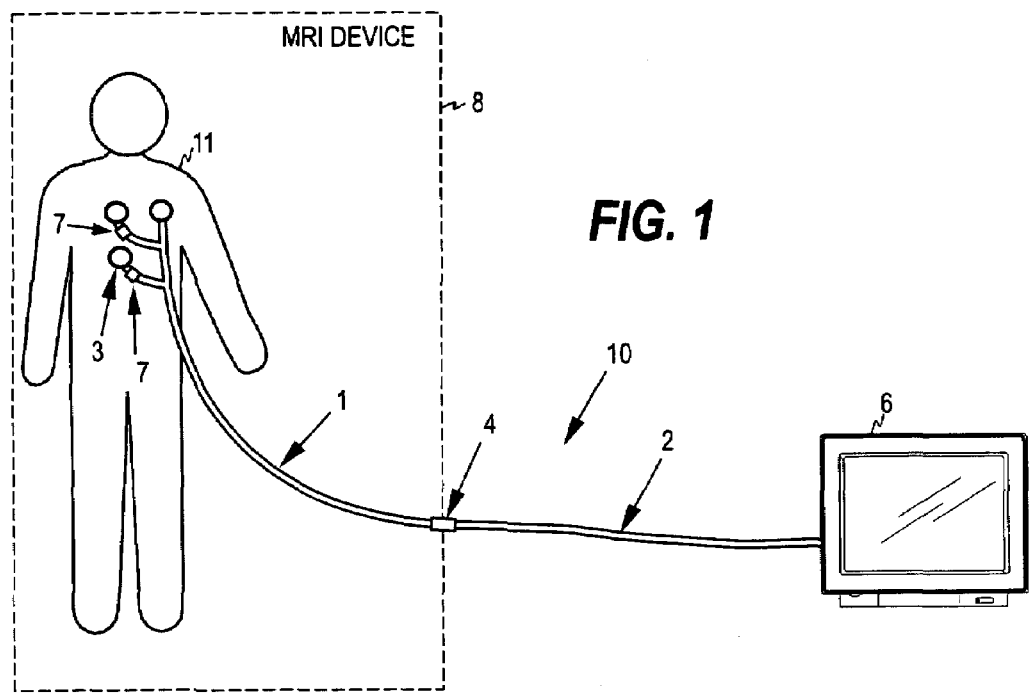
FIG. 1 illustrates the basic construction of the patient cable of the invention.

FIG. 1 illustrates the basic principle of a patient cable 10 according to the invention. The cable comprises two successive elements: a first cable element 1 that extends from patient 11 towards a monitoring device 6, and a second cable element 2 that connects the first cable element to the monitoring device located further away from the patient lying inside an MRI device 8.

The first cable element is at its first end connected to electrodes 3 attached on the skin of the patient. The length of the first cable element is dimensioned so that the first cable element forms substantially the part of the whole cable 10 that is inside the MRI device. The first cable element is at its second end connected to the first end of the second cable element 2. The mating connectors of the first and second cable elements are denoted with reference numeral 4. The second end of the second element is connected to the monitoring device that is apart from the MRI device. The said second end may be provided with a connector for connecting it to the monitoring device or the cable element may be integral with the monitoring device.

The total resistance of the first cable element 1 lying in a high RF field is made high enough so that the risk of injuries caused by electromagnetically induced patient currents and cable heating is eliminated. Although no exact values can be given for the resistance that is sufficient for this purpose, a good approximate value for the total resistance is the minimum value of 13 kOhms calculated in the above-mentioned article by Lemieux et al. Depending on the MRI set-up for which the cable is intended and on the safety margins used, the total resistance of the first cable element is preferably within the range of 10 to 100 kOhms, further preferably 15 to 60 kOhms, the resistance per unit of length being within the range of 5 to 30 kOhms/m. The length of the first cable element is typically between 1.5 and 3 meters, as it is preferable that the first cable element is substantially in its entirety inside the MRI device, the interface between the successive cable elements being substantially at the outer surface of the MRI device.

In one embodiment of the invention, the first cable element is provided with additional resistors 7 that can be integral with the connectors by which the first cable element is attached to the electrodes. The resistance per unit of length of the first cable element may then be lowered correspondingly.

As the purpose of the second cable element is to "extend" the first cable element to the monitoring device and simultaneously to prevent antenna resonances, the total resistance of the second cable element 2 is substantially greater than that of a normal high-conducting non-MRI patient cable. As the antenna resonance is achieved when the antenna is approximately half a wavelength long, the resistance needed can be estimated by comparing the second cable element to a half-wave dipole antenna. As is known, the radiation resistance $R_{rad}$ of a half-wave Hertz dipole antenna is about 73 ohms. Assuming that the radiation efficiency of the antenna must be below 0.5, in which case the antenna radiates less power than it dissipates in the form of heat, the resistance of the cable element should be then be more than said 73 ohms. In order to optimize the signal-to-noise ratio the resistance should also be as low as possible. However, since the above value of 73 ohms applies to a Hertz dipole and since in practice the radiation resistance of a wire antenna is higher, it is preferable that the total resistance of the second cable element is also higher. The fact that in practice the radiation resistance of a wire antenna is at most about 1 kOhms gives a good approximate value for the total resistance of the second cable element. Given that the practical radiation resistance of the cable element varies according to the cable geometry and the MRI environment and that different safety margins may be used, it may be stated generally that the total resistance of the second cable element is somewhere between about 70 ohms and a few kOhms, such as 3 kOhms. However, due to the above-mentioned reasons the resistance of the second cable element is preferably of the order of 1 kOhms, for example between 0.5 kOhms and 2 kOhms. Thus, the resistance of the second cable element is substantially lower than that of the first cable element, but also clearly higher than that of a high-conductive, non-MRI cable.

As the length of the second cable element is typically between 3 and 5 meters, the resistance per unit of length of the second cable element is typically within the range of 0.05 kOhms/m to 1 kOhms/m.

The patient cable of the invention may be manufactured as two separate pieces provided with mating connectors, as is shown above. In another embodiment of the invention, the first cable element is integral with the MRI device, whereby the MRI device may comprise a connector for the second cable element. As mentioned above, the second cable element may in turn be a separate piece provided with a connector at each end, or integral with the monitoring device. In a further embodiment, the patient cable is manufactured as a single cable comprising two successive elements permanently fixed together at the manufacturing phase.

Figure 2:
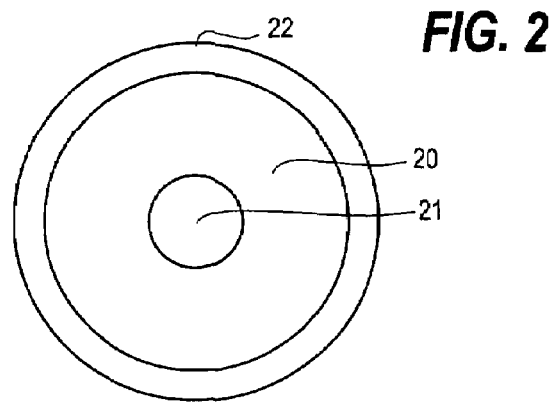
FIG. 2 is a cross-sectional view of one embodiment of the invention.

The actual structure of the cable elements may vary in many ways, since the above resistance characteristics may be achieved either by utilizing discrete resistor elements added along the length of the cable or by utilizing semi-conductive material in the conductor element of the cable, whereby the "extra" resistance can be evenly distributed along the length of the cable. One possible structure of the cable elements is shown in FIG. 2, which is a cross-sectional view of one of the cable elements. In this structure, the cable element comprises a conductor 20 provided with a longitudinal support 21 running along the center axis of the element. A sheath 22, made of polyurethane, for example, surrounds the conductor. In this structure, the conductor part is made of conductive non-metal material, such as a silicone compound to which carbon particles have been added evenly to produce conductivity. The resistance level of the cable element may then be adjusted by changing the relative amount of the carbon particles in the conductor part. A cable structure like this is shown in International Patent Application WO 01/97688.

Even though ECG measurements were used as an example of a measurement in MRI environment, the cable may be used in connection with any other measurements in the MRI environment. In fact, the present invention is even more beneficial in connection with EEG measurements, where the bioelectric signals are even weaker than in ECG measurements.

Although the invention was described above with reference to the examples shown in the appended drawings, it is obvious that the invention is not limited to these, but may be modified by those skilled in the art without departing from the scope and spirit of the invention. For example, other cable elements may be added between the second cable element and the monitor, or the induced RF currents may be further decreased by using additional reactance elements in the cable.

The invention claimed is:

1. A patient cable for use with magnetic resonance imaging apparatus generating an imaging field in which a patient is placed for imaging purposes, the patient cable conducting a bio-electric signal from a first end of the cable to a second end of the cable, the bio-electric signal being obtained from a patient electrode connectable to the first end of the patient cable and being supplied to apparatus connectable to the second end of the patient cable, said patient cable minimizing attenuation of the conducted bio-electric signal while suppressing the inductive generation of current and an RF antenna resonance effect in the patient cable during imaging thereby to minimize a risk of injury to the patient, the patient cable comprising:

a first elongated cable element having a first cable element end and a second cable element end, said first cable element end of said first cable element comprising said first end of the patient cable, said first cable element being in the magnetic resonance imaging apparatus when the patient is placed in the magnetic resonance imaging apparatus for imaging; and a second elongated cable element having a first cable element end and a second cable element end, said first cable element end of said second cable element being connected to the second cable element end of said first cable element, said second cable element end of said second cable element comprising the second end of the patient cable, said second cable element being generally outside the magnetic resonance imaging apparatus when the patient is placed in the magnetic resonance imaging apparatus for imaging;

said second cable element having a total resistance between its first and second ends sufficient to suppress an RF antenna resonance effect in the second cable element but insufficient to suppress inductively generated currents during magnetic resonance imaging, and said first cable element having a total resistance between its first and second ends substantially greater than that of the second cable element to suppress inductively generated currents, the patient cable minimizing both attenuation of the bio-electric signal and injury risks to the patient.

2. A patient cable according to claim 1, wherein the total resistance of the first cable element is within the range of 10 to 100 kOhms.

3. A patient cable according to claim 2, wherein the total resistance of the first cable element is within the range of 15 to 60 kOhms.

4. A patient cable according to claim 1, wherein the total resistance of the second cable element is within the range of 70 ohms to 3 kOhms.

5. A patient cable according to claim 4, wherein the total resistance of the second cable element is within the range of 0.5 kOhms to 2 kOhms.

6. A patient cable according to claim 1, wherein the length of the first cable element is shorter than that of the second cable element.

7. A patient cable according to claim 1, wherein the second cable element end of the first cable element and the first cable element end of the second cable element are provided with connectors for connecting said ends to each other.

8. An improved cable element for a two element patient cable used with magnetic resonance imaging apparatus generating an imaging field in which a patient is placed for imaging purposes, the other element of the patient cable being in the magnetic resonance imaging apparatus when the patient is placed in the magnetic resonance imaging apparatus for imaging and being subject to the inductive generation of current, said other cable element having a total resistance sufficient to suppress inductively generated currents, the improved cable element comprising:
an elongated cable element having a first end and a second end, said first end of said elongated cable element being connectable in series to the other cable element, said second end of said elongated cable element outputting a bio-electric signal, said elongated cable element being generally outside the magnetic resonance imaging apparatus when the patient is placed in the magnetic resonance imaging apparatus for imaging and being subject to an RF antenna resonance effect, said elongated cable element having a total resistance between its first and second ends substantially less than that of the other cable element and which is insufficient to suppress inductively generated currents but sufficient to suppress an RF antenna resonance effect in said elongated cable element during magnetic resonance imaging.

9. A cable element according to claim 8, wherein the total resistance of the cable element is within the range of 70 ohms to 3 kOhms.

10. A cable element according to claim 9, wherein the total resistance of the cable element is within the range of 0.5 kOhms to 2 kOhms.

11. A magnetic imaging system, the system comprising:
a magnetic imaging apparatus, the magnetic imaging apparatus generating an imaging field in which a patient is placed for imaging purposes;
a patient cable, the patient cable conducting a bio-electric signal from a first end of the cable located inside of the imaging field to a second end of the cable located outside of the imaging field, the bio-electric signal being obtained from a patient electrode connected to the first end of the patient cable and being supplied to apparatus connected to the second end of the patient cable;
the patient cable comprising
a first elongated cable element having a first cable element end and a second cable element end, said first cable element end of said first cable element comprising said first end of the patient cable, said first cable element located in the magnetic resonance imaging apparatus when the patient is placed in the magnetic resonance imaging apparatus for imaging; and
a second elongated cable element having a first cable element end and a second cable element end, said first cable element end of said second cable element being connected to the second cable element end of said first cable element, said second cable element end of said second cable element comprising the second end of the patient cable, said second cable element located outside the magnetic resonance imaging apparatus when the patient is placed in the magnetic resonance imaging apparatus for imaging;
a point of connection between said first and second cable elements located proximate an outermost boundary of the imaging field;
said second cable element having a total resistance between its first and second ends sufficient to suppress an RF antenna resonance effect in the second cable element but insufficient to suppress inductively generated currents during magnetic resonance imaging, and said first cable element having a total resistance between its first and second ends substantially greater than that of the second cable element to suppress inductively generated currents,
the patient cable minimizing attenuation of the conducted bio-electric signal while suppressing the inductive generation of current and an RF antenna resonance effect in the patient cable during imaging thereby to minimize a risk of injury to the patient.

* * * * *